United States Patent [19]

Polk et al.

[11] 4,226,239
[45] Oct. 7, 1980

[54] SURGICAL LIGATING INSTRUMENT AND METHOD

[75] Inventors: Todd J. Polk, Croydon; Francis E. McGowan, Abington, both of Pa.

[73] Assignee: KLI, Inc., Newtown, Pa.

[21] Appl. No.: 873,852

[22] Filed: Jan. 31, 1978

Related U.S. Application Data

[63] Continuation of Ser. No. 725,272, Sep. 21, 1976, abandoned.

[51] Int. Cl.³ .............................................. A61B 17/00
[52] U.S. Cl. ........................... 128/303 A; 221/312 A
[58] Field of Search .................. 128/1 R, 303 A, 325, 128/326, 327, 4, 6; 221/312 A, 65

[56] References Cited

U.S. PATENT DOCUMENTS

| | | | |
|---|---|---|---|
| 3,687,138 | 8/1972 | Jarvik | 128/326 |
| 3,967,625 | 7/1976 | Yoon | 128/326 |
| 3,989,049 | 11/1976 | Yoon | 128/326 |
| 4,103,680 | 8/1978 | Yoon | 128/326 X |

FOREIGN PATENT DOCUMENTS 1561218  2/1969  France .................. 128/326

Primary Examiner—Robert W. Michell
Assistant Examiner—Michael H. Thaler
Attorney, Agent, or Firm—Miller & Prestia

[57] ABSTRACT

A surgical ligating instrument is provided for tubal ligation within the human and/or animal body, by the application of two or more elastic rings to anatomical tubes such as Fallopian tubes. The instrument is constructed to grasp a Fallopian tube, to draw it into an elongated tubular member, and to discharge a stretched elastic ring on the Fallopian tube to perform the ligation procedure, followed by grasping the other Fallopian tube and discharging another similarly stretched elastic ring thereon, without removing the instrument from the patient's body.

70 Claims, 17 Drawing Figures

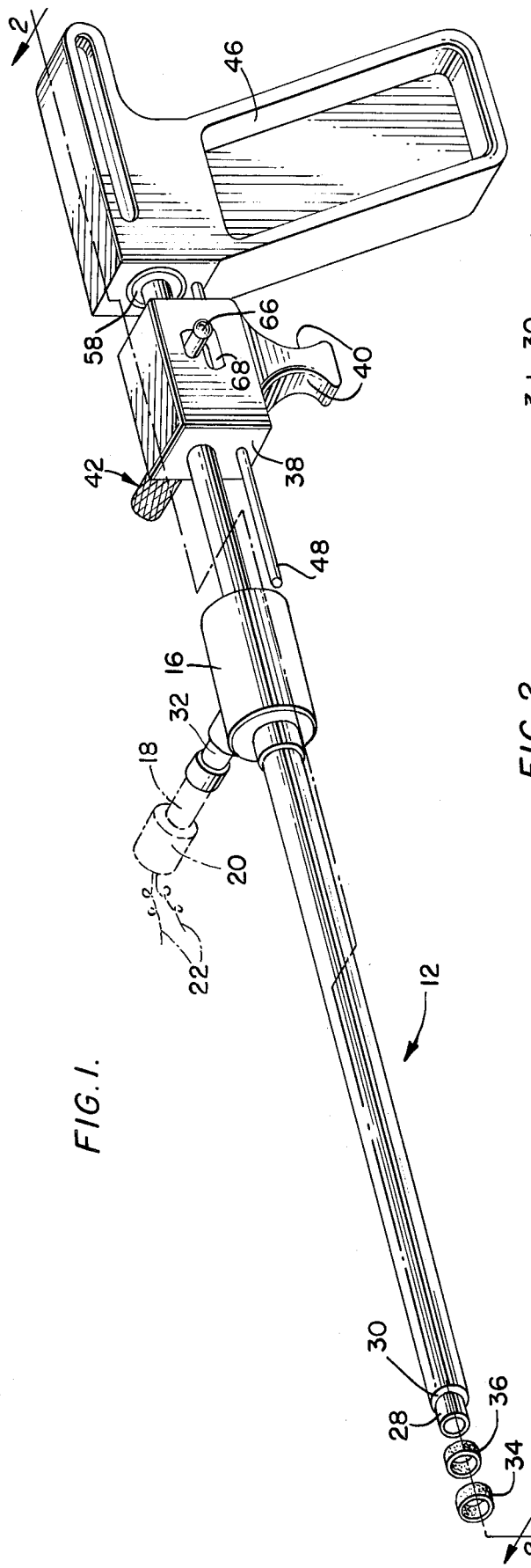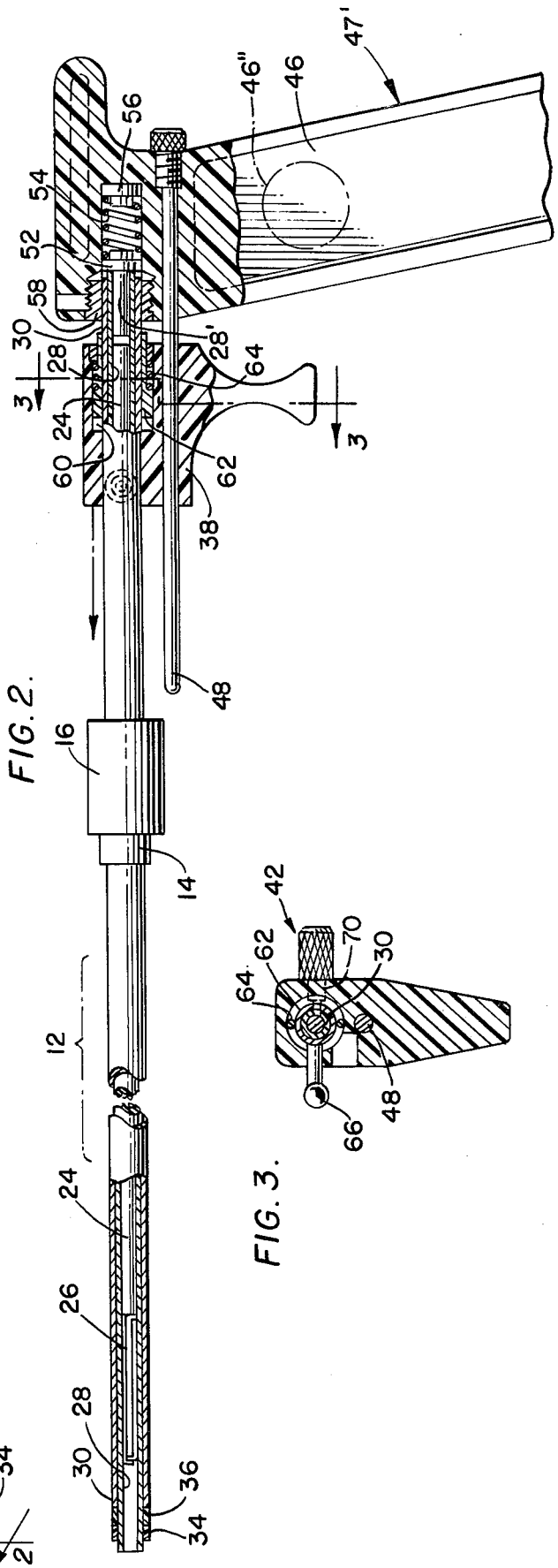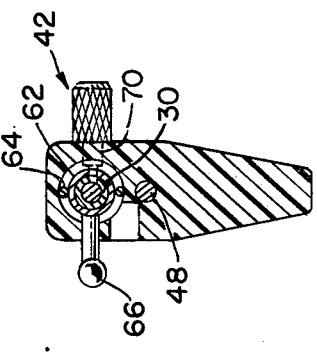

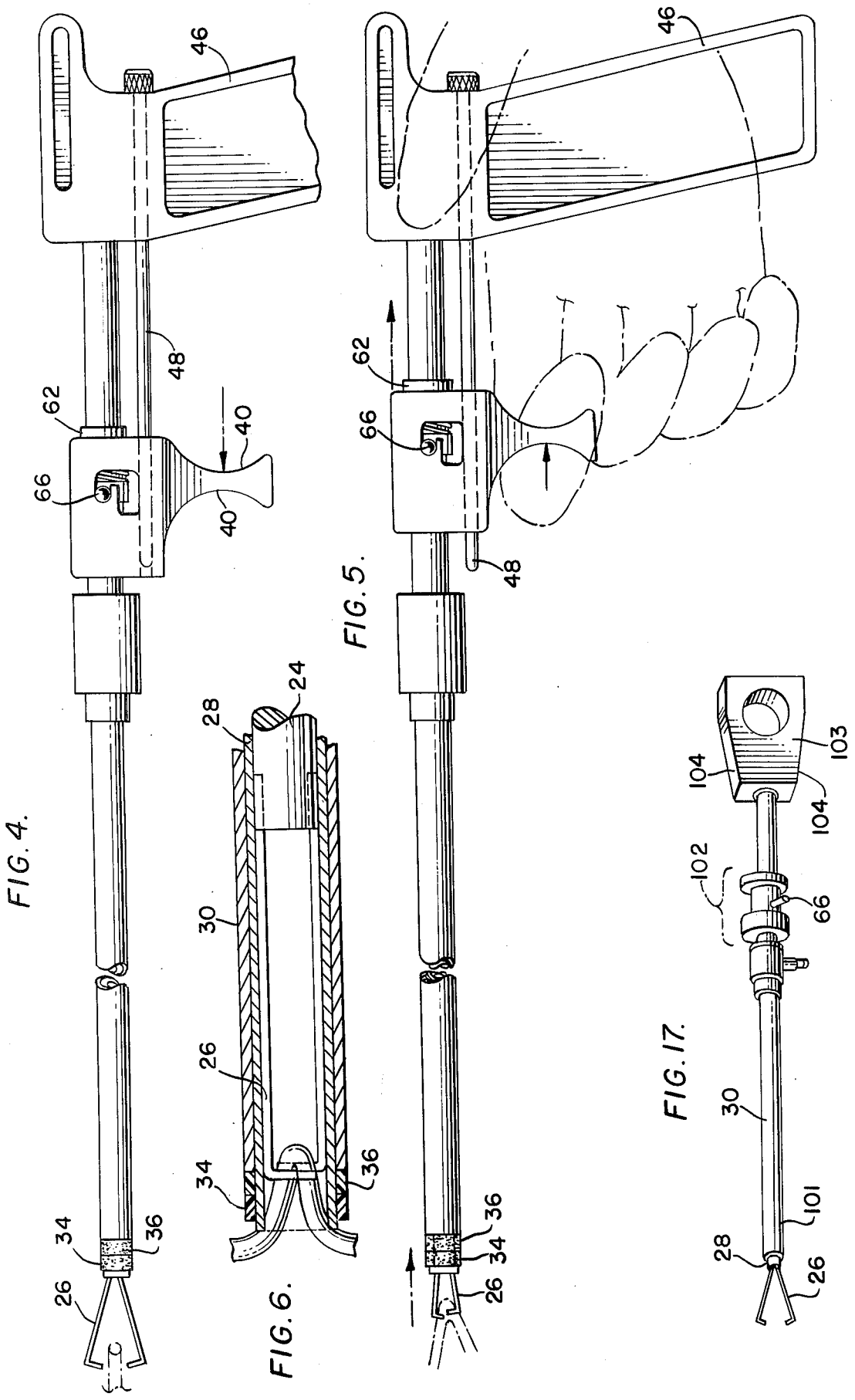

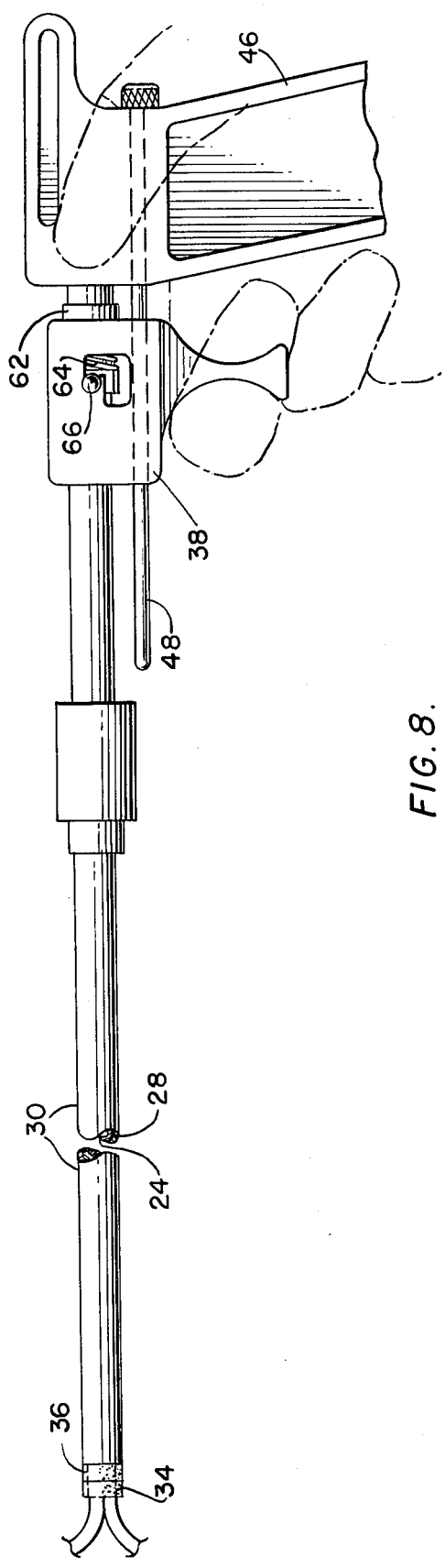
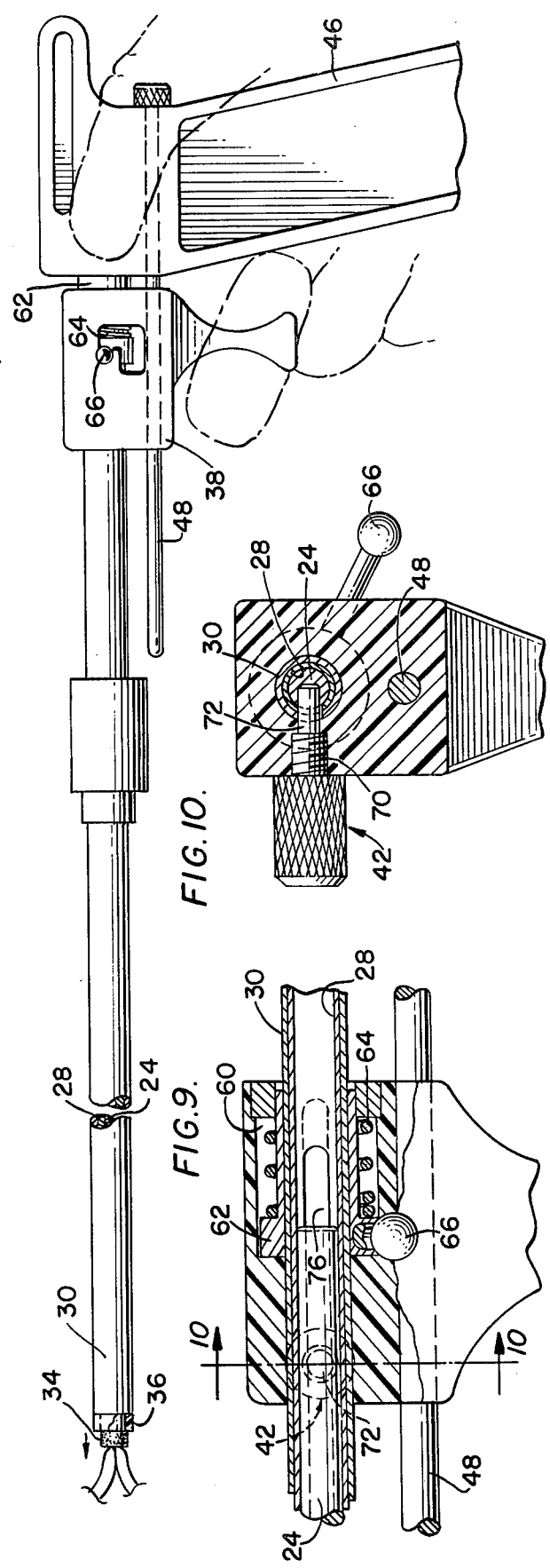
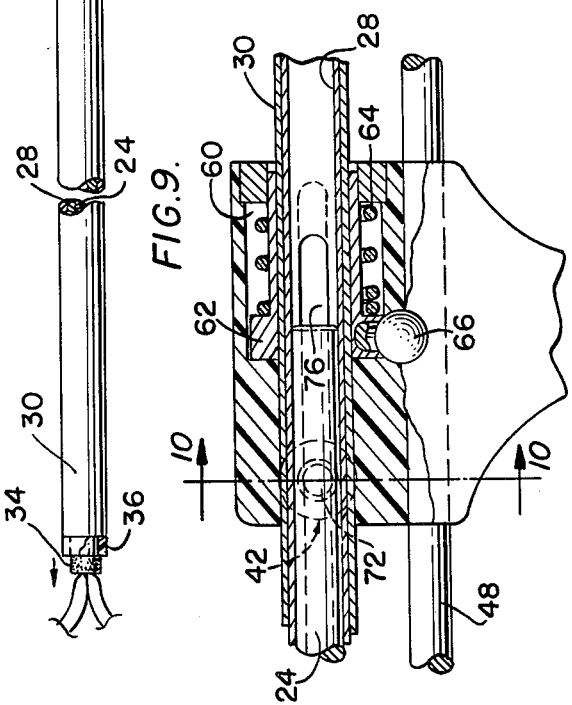

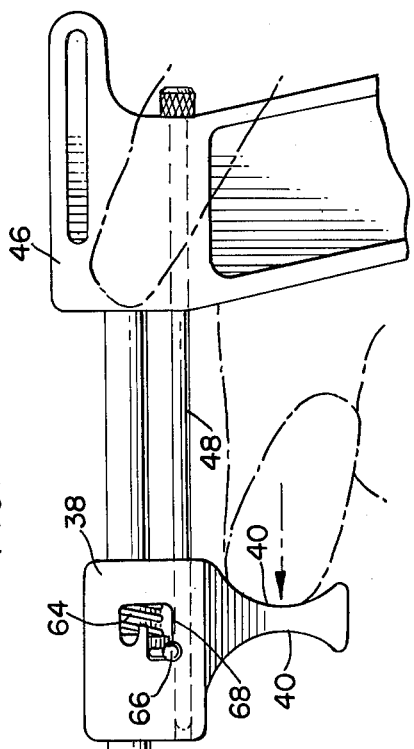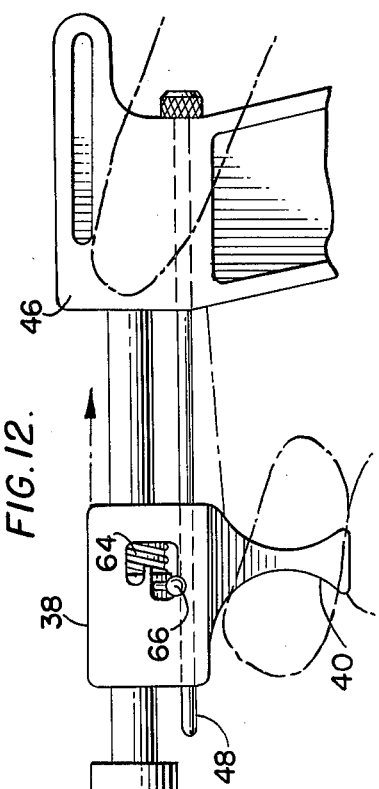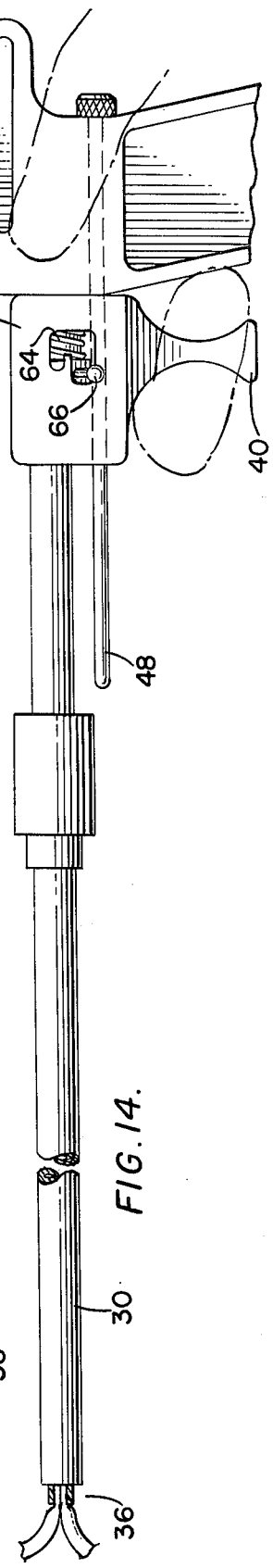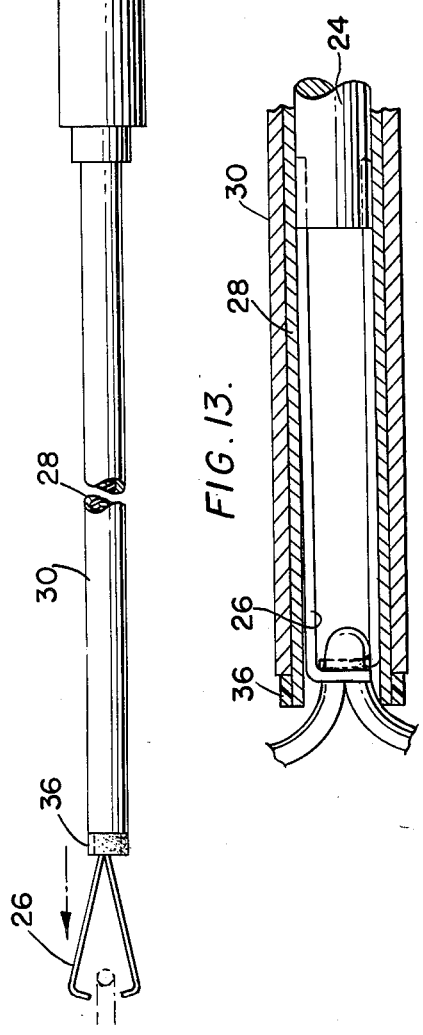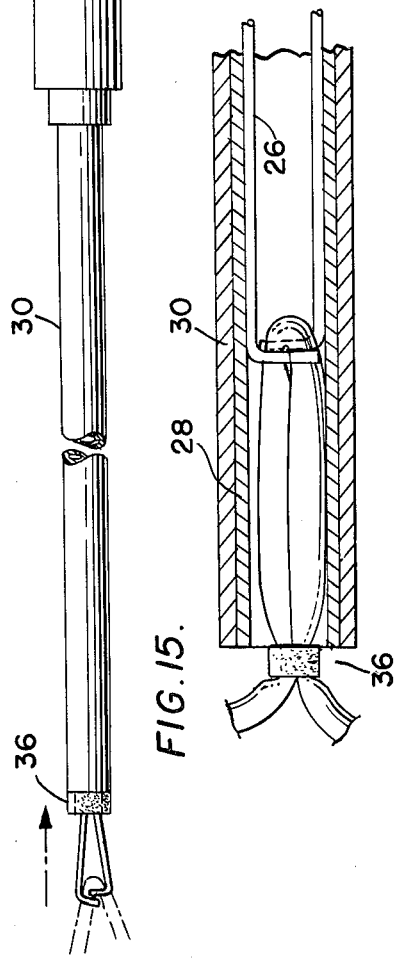

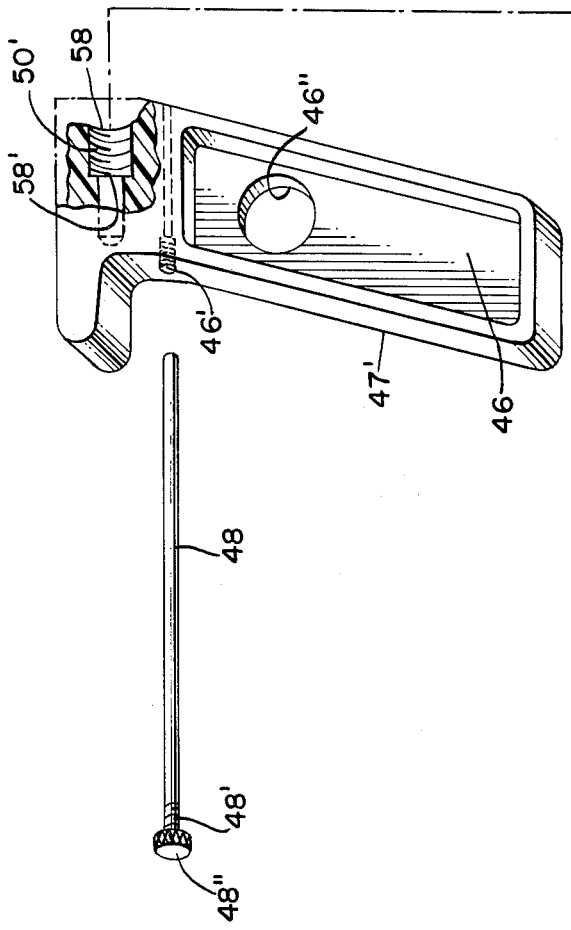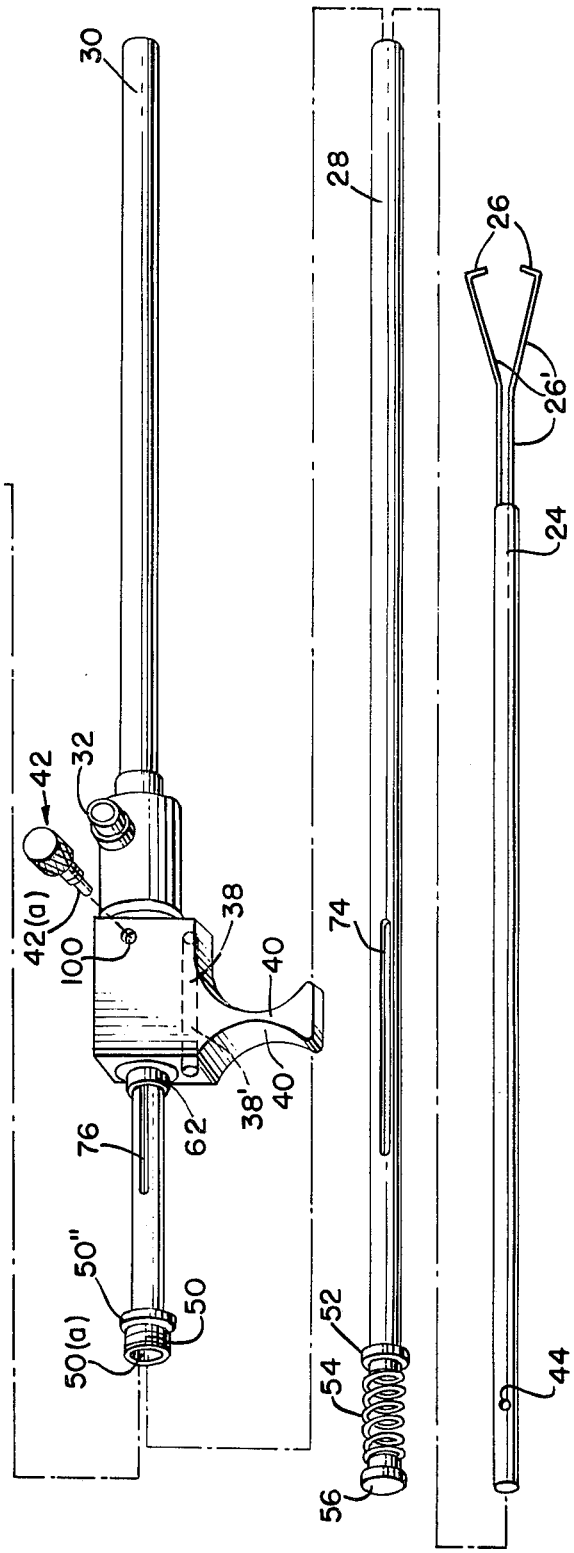
FIG. 16.

SURGICAL LIGATING INSTRUMENT AND METHOD

This is a continuation of application Ser. No. 725,272 filed Sept. 21, 1976, now abandoned.

The structure of the instrument causes performance of all of these steps in a single operative procedure, which may be conducted continuously.

A novel pistol grip and trigger are provided for actuating the release of the stretched elastic ring over and around the Fallopian tube.

The instrument is composed of a plurality of elongated members, cylindrical or tubular, which may be disassembled easily for effective cleaning and sterilization.

BRIEF DESCRIPTION OF THE INVENTION

This invention relates to a surgical ligating instrument or applicator for tubal ligation within the human and/or animal body, by the application of at least one elastic ring to an anatomical structure. Although this invention relates particularly to female sterilization procedures involving the Fallopian tubes, the instrument and method of this invention may be applied to one or a plurality of vas in the human male, and to any other anatomical structural member.

The surgical ligating instrument in accordance with this invention may be used ideally in minilaparotomy in alternative with single and dual incision laparoscopy. It can be used in combination with a laparoscopy system of the type described in the issued U.S. Patent to Lampman and Knepshield U.S. Pat. No. 3,834,392. In the alternative, it may be used in a two-incision operation, or in minilaparotomy in a supra-public type of operation. The instrument in accordance with this invention is relatively simple and inexpensive in construction, and requires a minimum of maintenance. Of greater importance, however, is the fact that it is extremely convenient and effective for the surgeon to handle, particularly in allowing the surgeon to perform the most delicate and critical steps of the procedure smoothly and continuously and, if desired, for applying successive rings without removing the instrument from the body cavity. It operates smoothly and continuously and eliminates possible misjudgment on the part of the physician as to size of loop and tension on the Fallopian or other tube—which factors are set by the applicator and the ring.

As will further become apparent hereinafter, the instrument and method in accordance with this invention are of particular advantage in that heretofore the surgeon, after performing one step of the method by applying one ring to one of the Fallopian tubes, has been required to remove the applicator from the body cavity and apply another elastic ring to the applicator before he could perform the further step of the procedure in which the applicator is re-inserted into the body cavity and the other ring is stretched over the other Fallopian tube.

DISCUSSION OF THE PRIOR ART

Surgical ligating instruments have heretofore been used for a wide variety of purposes.

In the prior U.S. Patent to Lampman and Knepshield U.S. Pat. No. 3,834,392 granted Sept. 10, 1974, a laparoscopy system is disclosed for female sterilization, whereby a single unit contains a power source to provide illumination, oscillatory electrical power and $CO_2$ for a laparoscopy. $CO_2$ gas, under pressure, is first passed into the body through a needle into the peritoneal cavity. A trocar and cannula are inserted into the gas-filled abdominal cavity. A laparoscope connected to a source of illumination is inserted into the body cavity through the cannula. The Fallopian tubes are then identified through the laparoscope. A flexible forceps is, thereafter, inserted through the laparoscope into the body cavity. The forceps is manipulated to successively close the passage through each Fallopian tube either by means of sending electrical oscillations through the forceps to simultaneously cut, seal and cauterize each tube in turn, or by means of a specific clamp which clamps the passage shut.

A typical clamp for that purpose is described in the U.S. Patent to Davis U.S. Pat. No. 3,856,016, granted Dec. 24, 1974.

Still another clamping means utilized in tubal ligation, having the form of an elastic cord or ring, is shown and described in the U.S. Patent to Van Hoorn U.S. Pat. No. 3,760,810, granted Sept. 25, 1973. The Van Hoorn patent shows a surgical instrument for ligating internal structures of a cavity in the human body, by means of at least one elastic cord. Two tubes are mounted for relative sliding movement one inside the other, the inner tube protruding at the front of the outer tube. An elastic cord or band is stretched upon the outer surface of the protruding portion of the inner tube, and after the tube to be ligated is drawn into the inner tube of the surgical ligating instrument, relative displacement of the outer tube forwardly relative to the inner tube ejects the elastic band and tightens it about the tube to be ligated. Thus, a stretchable or elastic cord or ring is used in the manner of the clamp of the Davis patent, for tubal ligation of blood vessels in the treatment of rectosigmoidal lesions, and in the treatment of internal structures of the human body.

The use of an elastic band or ring in tubal ligation of the Fallopian tubes in the human female, or the vas in the human male, using the system of the aforesaid U.S. Pat. No. 3,834,392 is shown in the U.S. Patent to Yoon U.S. Pat. No. 3,870,048, granted Mar. 11, 1975. In the Yoon device, as well as in the aforesaid patent, the procedure is preferably used in conjunction with a viewing device such as an endoscope or laparoscope for example. The placement of the elastic ring on the tubes eliminates the need for time-consuming procedures which are discomforting to the patient and the use of bulky and expensive equipment. Moreover, depending upon the size and elastic power of the rings, the sterilization can be made permanently or reversibly, as desired. The device and method are also applicable to the sterilization of the human male by the ligature of the vas. Further, the device of the Yoon patent includes an outer tube having an expandable end portion which permits the device to be "loaded" with two or more rings at the same time, and to discharge separate rings at different times and in succession to one another, so that both Fallopian tubes may be successively ligated without removing the ring applicator device from the peritoneal cavity of the patient.

The devices of the prior art, as discussed herein, tend to be rather complicated for the surgeon to operate. The ejection of multiple rings in succession, for example, as in the Yoon patent, requires a considerable number of successive manipulations in order to grasp the Fallopian tube, draw it into the inner tube of the instrument, and discharge each elastic ring to its desired position surrounding each Fallopian tube. Also, substantial gas pressure losses are encountered, requiring monitoring and replacement of gas escaping from the peritoneal or other cavity.

In a copending application of Messrs. Lampman and Knepshield, Ser. No. 605,187 filed Aug. 15, 1975, a special applicator is provided having a novel means for providing minimum resistance to the movement of the surgeon's hand while the Fallopian tube is being drawn into the tubular member of the surgical instrument, and for providing increased resistance after the foregoing step has been completed and prior to the step of releasing the elastic ring. Also, the aforesaid application discloses a plurality of elongated cylindrical or tubular members, slidable axially with respect to each other to perform the tubal ligation operation, and which cylindrical or tubular members may easily be disassembled for effective cleaning and sterilization. However, an instrument of the type disclosed in the aforesaid pending application is adapted for the discharging of a single ring upon a single Fallopian tube, and must be removed from the body cavity of the patient for the purpose of stretching another ring over the cylindrical applicator tube, in order to prepare the instrument for reinsertion into the body cavity and for discharging the added elastic ring into a position in which it is stretched around the other Fallopian tube within the body of the patient.

It is accordingly an object of this invention to provide a multiple ring applicator which discharges successive rings around successive Fallopian tubes, all without removal from the body cavity.

Still another object of this invention is to provide a device for successive stretching of successive rings around successive Fallopian tubes within the human body, wherein the degree of stretch applied to each ring is essentially the same as the degree of stretch applied to the other ring.

It is another object of this invention to provide a ring applicator which is easy to manipulate in the performance of the surgical procedure, and which quickly and effectively accomplishes the desired result.

It is still another object of this invention to provide a ring applicator which is easy to take apart, clean, sterilize and assemble.

Still another object is to provide a surgical instrument having a plurality of moving parts capable of performing a tubal ligation procedure while maintaining a pressurized gas condition within the cavity in which the procedure is taking place, all without excessive gas pressure loss from said cavity.

Other objects and advantages of the invention will further become apparent hereinafter, and in the drawings, of which:

DRAWINGS

FIG. 1 is a perspective view of a ligating instrument embodying features of the present invention;

FIG. 2 is a side elevational view of the instrument indicated in FIG. 1, with certain parts shown in section in order to illustrate important details, taken along the lines and arrows 2—2 which appear in FIG. 1;

FIG. 3 is a sectional view taken along the lines and arrows 3—3 as indicated in FIG. 2;

FIG. 4 is a side view of the same embodiment as FIG. 2, illustrating the manner in which the grasping means may be manipulated to grasp the anatomical tube to be ligated;

FIG. 5 is a similar side view, showing a subsequent operational step involving the rearward movement of the grasping means into the inner tube member;

FIG. 6 is a detailed sectional view of the forward end of the instrument of FIG. 1, showing an anatomical tube being drawn into the forward end portion of the inner tube member;

FIG. 7 is a side view similar to FIG. 5, illustrating commencement of the rearward movement of the inner tubular member;

FIG. 8 is a side view similar to FIG. 7, illustrating a subsequent step involving the ejection of one occluding ring from its position around the inner tube member as the stop member abuts the pistol grip;

FIG. 9 is a detailed view, partially in section, of a portion of the instrument of FIG. 1, showing one form of an adjusting means used to adjust the effective position of the stop member;

FIG. 10 is a sectional view taken along the lines and arrows 10—10, which are indicated in FIG. 9;

FIG. 11 is a side view similar to FIG. 8, illustrating a further manipulative step involving the forward displacement of the trigger to move the grasping means forwardly from the elongated inner member so as to grasp another anatomical tube to be ligated;

FIG. 12 is a side view similar to FIG. 11, illustrating another step of the method, involving the rearward movement of the grasping means toward the inner tube member;

FIG. 13 is a detailed sectional view of the forward end portion of the applicator, showing the anatomical tube being drawn within the inner tube member;

FIG. 14 is a side view similar to FIG. 11, showing a further step of the method involving maximum rearward withdrawal of the inner tubular member in relation to the outer tube, so that a second occlusion ring will be ejected over the same or another anatomical tubular structure;

FIG. 15 is a detailed sectional view of the forward end portion of the applicator after the inner tube member has been rearwardly drawn into the outer tube so as to place the occlusion ring about the desired anatomical tube; and FIG. 16 is an exploded view of the applicator of FIG. 1, and FIG. 17 is a view in perspective of an alternative embodiment of the invention (rings not shown).

DETAILED DESCRIPTION OF THE PREFERRED EMBODIMENTS

Although in the description which follows specific terms will be used for the sake of clarity in describing the specific form of the invention selected for illustration in the drawings, it will be appreciated that the use of these terms is not intended to define or to limit the scope of the invention, but is intended to apply only to one specific form thereof, as shown in the drawings.

Referring now in detail to the Figures of the drawings, wherein similar reference numerals refer to similar parts, and turning to FIG. 1, there is shown one form of applicator of the present invention. The number 12 designates a ligating instrument in accordance with this invention. Instrument 12 includes tubular portion 16, fiber optic connector 32, and a source of light 20 which can be wired with wires 22 to deliver light through a fiber optics system as is known per se.

As shown in FIG. 1, elastic ligating or occlusion rings 34, 36 are stretched over the forward end portion of inner tube member 28 in a side-by-side fashion so that the rings may be sequentially ejected therefrom. This is an important feature of this invention since both rings are subjected to substantially exactly the same degree of stretch, the outside diameter of the end of inner tube 28 being substantially uniform.

The ligating instrument of the present invention may be utilized with or without an endoscope operatively connected therewith. Indeed, it may be desirable for the surgeon to perform a single incision operation wherein applicator and endoscope are operatively combined. Such an operation and apparatus therefor are shown in U.S. Pat. No. 3,834,392 of common assignment herewith.

Moreover, the applicator, subject of the present invention, may be utilized in a two-incision operation wherein the applicator and endoscope, as separate instruments, enter the body cavity through different incisions. Also, the applicator may be utilized with a light source but no optics, in a supra-public operation.

Turning next to FIG. 16 of the drawings, wherein the components are shown separately in the interest of clarity, the applicator includes an elongated rod member 24 that has grasping means, such as forceps 26, located at the forward end portion of rod 24. Forceps 26 are designed to grasp an anatomical tube, such as a Fallopian tube in a female, or the vas in the male, to be ligated. Inner tube member 28, having an inside diameter only slightly larger than the outside diameter of rod 24, fits slidably over rod 24 in such a manner that rod 24 may be slidably drawn inside of inner tube member 28 while gas cannot escape in significant amounts between these two elongated members.

In turn, elongated fiber optic outer tube member 30, in like manner, snugly but slidably fits over inner tube member 28 so that significant amounts of gas may not escape between the inner and outer tubes. As will further become apparent hereinafter, when the applicator is assembled, the forward edge portion of outer tube 30 is spaced rearwardly in relation to the forward edge portion of inner tube member 28, providing a protruding portion upon which one or more elastic occlusion rings may be loaded.

An extension 32 is provided, and contains a bundle of fiber optic strands which bend forwardly in tubular portion 16 and extend to the forward end of tube 30, which parts are themselves well known, and are accordingly not shown, wherein the extension is adapted to be connected to a light source or a light transmitting cable which also comprises a bundle of fiber optic strands encased in a flexible sheathing, for example, adapted to be connected to an illuminator in the manner fully shown and described in aforementioned U.S. Pat. No. 3,834,392.

Light transmitting means, such as fiber optic strands, may be placed within a bore located in rod 24, or in inner tube 28. Also, rod 24, or tube 28 can be used as an optical viewing tube, reference being made to the aforesaid U.S. Pat. No. 3,834,392. The fibers are located in outer tube 30, as heretofore discussed.

Push-pull trigger housing 38, having oppositely faced concave trigger surfaces 40, 40 depending therefrom, is mounted for back and forth reciprocation on outer tube 30. Connector rod 42 extends through and is threaded to an aperture (not visible in FIG. 1, but indicated as 100 in FIG. 16) formed in a side wall of housing 38, and fits through aligned slots 76, 74 (see FIG. 16) which will be described in further detail hereinafter, but which are formed in outer tube 30 and inner tube 28, respectively. The rod 42 accordingly projects into bore 44 (FIG. 16) formed in the rearward end portion of rod 24 and has a non-threaded end 42(a) extending therein. In this manner, housing 38 is reciprocably drivingly connected directly to rod 24, through contact between non-threaded end 42(a) and the inner wall of bore 44. Bore 44 and slots 76, 74 are aligned.

As is seen in FIG. 16, a guide rod 48, adapted to be spaced parallel to outer tube 30, is adapted to be slidably disposed through bore 38 of trigger housing 38 and to be threadedly anchored at its rearward end in threaded opening 46' in pistol grip member 46. The pistol grip member 46 may be a solid, unitary assembly, or it may include a hole 46" shown in dotted lines bored therethrough and adapted to accommodate the surgeon's thumb. As shown in FIG. 16, the pistol grip has a substantially flat rearward surface 47' so that the surgeon's palm may bear against this surface area.

As best seen in FIG. 16, the rearward end portion of outer tube 30 carries a threaded adapter 50 which is threaded into a corresponding threaded aperture 50' formed in the pistol grip member 46 (FIG. 16). A collar 52 is formed at the rearward end portion of inner tube member 28, and is arranged to abut forwardly against the rear surface of threaded adapter 50. Projecting from the rear end portion of inner tube collar 52 is a helical compression spring 54 that is secured to a slug 56 which in turn is arranged to abut against a dead end 58' in bore 58 of pistol grip member 46.

The manner in which the individual components of FIG. 16 are connected to each other will now become apparent. The rod 24, with forceps 26, is slid rearwardly into inner tube 28 until the forceps 26 are closed and positioned completely within the inner tube 28. (The forceps 26 and their leg portions 26' are preferably staggered slightly with respect to one another, and pass closely adjacent to each other when they are closed.) The bore 44 is, of course, aligned with slot 74 of inner tube 28.

The resulting sub-assembly is then inserted forwardly through the rearward end (50) of outer tube 30, taking care that bore 44 and both slots 74 and 76 are aligned. Forward movement is continued until flange 52 of inner tube 28 contacts the rearward surface 50(a) of threaded adapter 50. Threaded bore 100 of housing 38 is then aligned with bore 44 of rod 24, by suitable rotation and positioning of housing 38, and the threaded driving connector 42 is threaded securely into bore 100, with its unthreaded end 42(a) extending into bore 44.

The pistol grip 46 is then threaded directly to the outer tube 30 by inserting slug 56, spring 54 and collar 52 of inner tube 28 into the threaded opening 50' of pistol grip 46, with threaded connector 50 of outer tube 30 threadedly engaged in threads 50' of pistol grip 46. By relative rotation of the outer tube 30 and pistol grip 46, this threaded connection is secured and tightened, thus bringing the end of slug 56 into contact with the blank end wall 58' of threaded opening 50'. The bore 46= of pistol grip 46 is then lined up with the bore 38' of housing 38, and the guide rod 48 is inserted forwardly through both bores, and threaded portion 48' is screwed into threaded opening 46' with the use of knurled head 48" of guide rod 48.

With particular reference to FIG. 2, a stop means is shown in detail, and comprises an important feature of this invention. A portion of trigger housing 38 is hollowed around the outer circumference of outer tube 30 to form an adjustment channel 60. Inserted about outer tube 30, and within adjustment channel 60, is a stop sleeve 62. Stop sleeve 62 is urged toward the forward end of ligating instrument 12 by the action of a coiled compression spring 64 that surrounds the middle portion of sleeve 62. Stop adjustment handle 66 (See FIG. 1) is firmly secured to, or is an integral part of, stop sleeve 62. By manually engaging handle 66 and moving it to the lower and forwardmost position in slot 68, (as shown in FIG. 11), stop sleeve 62 is drawn entirely within trigger housing 38. By placing the stop adjustment handle in its upper and forward position as shown in FIG. 1, the rear end of sleeve 62 protrudes from the rearward end portion of the trigger housing (FIG. 2). Normally, the stop sleeve and adjustment apparatus are aligned in such manner that the stop sleeve can be made to halt the rearward movement of the trigger by being adjusted to different incremental positions. These different incremental stop positions may desirably be spaced apart from each other at a distance that is approximately equal to the width of an occlusion ring.

As has been previously stated, connector 42 is carried by the reciprocating motion of trigger housing 38 along outer tube 30 and guide 48. As appears in FIGS. 3 and 10, connector member 42 contains a threaded portion 70 that securely anchors the connector to the trigger housing. Stud portion 42(a) fits through aligned channels 74, 76 (FIG. 16) formed in the inner and outer tubes respectively and is threaded through aperture 44 drilled in the rear end of rod member 24.

OPERATION

In order better to describe the operation of ligating instrument 12, reference will be made to its use in the occlusion of the Fallopian tubes of a female patient. It should be remembered that such reference is for illustrative purposes only, as the novel apparatus of the present invention may be utilized to ligate any anatomical tubular structures. Therefore, the description of the operational aspects of the invention should be construed as being descriptive only, and not limiting in any manner whatsoever. In referring to the sequence of steps performed, FIGS. 1, 2, 4, 5, 7, 8, 11, 12 and 14 may be considered as illustrative of typical steps as performed by the surgeon in performing ligation procedures on two Fallopian tubes without removing the instrument from the incision.

As may be seen in FIG. 1, occlusion rings 34, 36 are loaded onto the forward edge portion of inner tube member 28 in a side-by-side fashion. Accordingly, it will be seen that the length of the surface of the forward end portion of inner tube 28 that protrudes from outer tube 30 must equal at least N×W (wherein N is equal to the number of occlusion rings to be loaded about the inner tube and W is equal to the width of an occlusion ring).

Before starting, the surgeon should make sure that adjustment handle 66 is at its top uppermost position in adjustment slot 68 as may be seen in FIG. 1, so that the rear end portion of stop sleeve 62 protrudes a predetermined distance (as shown in FIG. 2) approximately equal to the width of one occlusion ring) from the rear of trigger housing 38. After suitable incision, insufflation of the abdominal cavity (if applicable) and insertion of the instrument, the surgeon displaces the concave trigger face forwardly with the front portion of his index finger, shifting the forceps 26 from the FIG. 2 to the FIG. 4 position. Rod 24 is caused to move forwardly as in FIG. 4 with respect to both the inner and outer tubular members, due to the threaded engagement of screw 42, carried by housing 38, in aperture 44 bored in the rear end portion of rod 24, as previously described in connection with FIG. 16.

As seen in FIG. 4, forceps 26, being made of a spring-biased metal, open automatically upon forward displacement from the confines of inner tube 28. When a Fallopian tube has been grasped, as in FIG. 5, the surgeon slowly pulls the trigger toward pistol grip member 46, as indicated by the arrow in FIG. 5 Due to the engagement of screw 42 in aperture 44, rod 24 with associated forceps 26 is rearwardly withdrawn inside inner tube 28, as seen clearly in FIGS. 5 and 6.

A portion of FIG. 2 has been broken open to illustrate further details of internal construction, showing how the rearward movement of trigger housing 38 actuates the release of an occlusion ring from the forward end of inner tube 28. The rearward movement of the rearward end of rod 24 is accomplished without spring resistance while the Fallopian tube is being doubled over and drawn into the forward end of inner tube 28, until the rearward end of rod 24 contacts a semi-cylindrical stop insert 28' located in a fixed position within the rearward end of inner tube 28. Further retraction, after such contact, causes rod 24 to displace inner tube 28 rearwardly relative to outer tube 30. This displaces both rings 36, 34 forwardly of the front end of inner tube 28, ultimately ejecting the first occlusion ring 34.

The length of stop insert 28' is carefully predetermined so that rearward driving movement of inner tube 28 is caused only by contact between rod 24 and stop insert 28', and not by contact of pin 42(a) against the end of slot 74.

Accordingly, retraction of trigger 38 first causes rearward movement of rod 24 when the trigger is pulled, followed by subsequent rearward movement of inner tube member 28 as in FIG. 8 after the rod 24 has been withdrawn a predetermined distance. Thus, the surgeon, when pulling the trigger rearwardly, initially meets little resistance as inner rod member 24 is rearwardly withdrawn as in FIG. 7. However, when the rearward pull continues, as in FIG. 8, the surgeon feels an increase in resistance when rearward motion of inner tube 28 is commenced, due to the compression of the spring 54. Thus the surgeon, upon feeling resistance, easily knows when an occlusion ring is about to be ejected from the forward edge portion of inner tube 28.

Stop sleeve 62, due to the placement of stop adjustment handle 66, protrudes rearwardly from trigger housing 38. As the stop sleeve abuts pistol grip 46 (see FIG. 8), one occlusion ring 34 is pushed by the second occlusion ring 36, which in turn is pushed by the front edge of outer tube 30. In this way, ring 34 is ejected from its position about the outer circumference of inner tube 28 by the rearward withdrawal of rod 24 and inner tube 28 into outer tube 30. Concurrently, the second ring 36 is shifted forwardly by the front edge of outer tube 30 through a distance essentially equal to the width of ring 34. The rearward limit of the surgeon's pulling action, caused by the abutment of stop sleeve 62 with the front end portion of pistol grip member 46, signals the physician that one occlusion ring has been ejected around the patient's Fallopian tube.

Without withdrawing the instrument from the body cavity, the surgeon pushes the trigger forwardly with the forwardly facing surface of his index finger, as in FIG. 11, to expel the now occluded Fallopian tube from the inner tube 28, thus causing the forceps 26, 26 forwardly until they are free to spring open to release the Fallopian tube. Helical spring 54 urges inner tube 28 forwardly during the first part of this forward movement without the additional help from the surgeon's index finger.

To adjust the instrument for placement of the second ring 36, the surgeon places stop adjustment handle 66 in its lower and forwardmost position as illustrated in FIGS. 9, 11, 12 and 14. Thus, the stop sleeve 62 is pushed to its forwardmost position within adjustment channel 60 so that the rear end portion of the sleeve 62 is shifted forwardly through a distance essentially equal to the width of a ring. As shown, sleeve 62 is so shifted as to be totally disposed within trigger housing 38.

The surgeon, after locating the other Fallopian tube, then rearwardly pulls trigger 40 toward pistol member 46 as shown in FIGS. 12 and 13. During rearward withdrawal, the spring-biased forceps close in response to the confining action of inner tube 28 and gently draw the doubled Fallopian tube inside the inner tube 28. Subsequent pulling of the trigger 38 causes the inner tube 28 to move rearwardly with respect to the outer tube 30, as in FIG. 14. Again, the surgeon feels an increase in resistance to his pull. Since the stop sleeve 62 does not protrude rearwardly from the trigger housing, due to the forward placement of the stop adjustment handle 66, the second occlusion ring 36 is ejected as in FIGS. 14 and 15 when, or slightly before, the trigger housing 38 abuts pistol grip 46.

The surgeon then, after feeling the stop action due to trigger housing contacting the pistol grip, knows that the second occlusion ring 36 has been ejected, and accordingly moves the trigger forwardly to expel the now occluded second Fallopian tube from the applicator in a manner similar to that appearing in FIG. 8. As previously mentioned, spring 54 urges the inner tube forwardly during part of this step.

Upon completion of the method steps just described, both Fallopian tubes are occluded and the operation may be completed by withdrawing the instrument and closing the incision. It should be noted that the applicator of this invention can be utilized to place a plurality of occlusion rings about the same or different anatomical structure and that more than two rings may be applied as will now be apparent.

It will be appreciated that, however used, and whether used in conjunction with an endoscope or not, the operation of the ligating instrument 12 is extremely simple, even in the hands of a surgeon who is relatively inexperienced in this ligation procedure. Due to the action of spring 54 and the stop sleeve 62 and its associated adjustment handle 66, the surgeon is automatically informed at the stage when the forceps 26 have been withdrawn completely into the inner tube 28, and when the instrument is ready to discharge, and has discharged, an occlusion ring.

FIG. 17 shows an alternative embodiment of this invention, with an integral fiber light guide 101 on outer tube 30, but without optics. Instead of a trigger a flanged finger grip 102 is provided, and may be structurally similar to trigger 38 as regards stop means adjustment for precision ejection of successive occlusion rings. Instead of pistol grip 46 a thumb grip 103 is provided, having gently sloped walls 104, 104, which are helpful in operation since the surgeon will not hit them with his fingers while withdrawing finger grip 102 toward thumb grip 103.

Of course, a wide variety of equivalent elements may be substituted for those specifically shown and described. For example, any sort of stop means may be provided, instead of the stop means provided in a hollowed portion of the trigger housing. Further, any resistance supplying means may be substituted for the compression spring 54 that is housed in the pistol grip member.

It is important that a close sliding fit may be maintained along the rod 24, the inner tube 28 and the outer tube 30. As has been noted, the ligation procedure is frequently performed while maintaining a certain required gas pressure inside the abdominal cavity of the patient. While loss of gas pressure can be readily made up, and is indeed normally made up in the course of the usual tubal ligation procedure, it is highly preferred to maintain such close clearances that, although they do not interfere with relative sliding movement, they do very substantially reduce the escape of gas between the relative sliding surfaces.

It will now be apparent that the instrument in accordance with this invention is very easy to disassemble, clean, sterilize and reassemble. As viewed in FIG. 16, the separate parts contain mostly open and easily accessible surfaces. Although it is preferred to clean and sterilize the parts separately, they can be cleaned separately, and then reassembled and sterilized. Difficulty in sterilization has been a serious drawback in instruments of the prior art.

It is highly recommended that the applicator should be cleaned immediately after use. This is done by placing the disassembled applicator parts and a cleaning brush in warm water with a mild, not abrasive detergent. A brush may be utilized to clean the insides of the tubes, and it is preferably pushed into the tubes using a rotating motion. When cleaning the outer tube 30, a brush can be pushed through until the bristle portions project from the tube.

After cleaning, the outside of the tubes are simply wiped off with a soft cloth and the parts are rinsed thoroughly with clean water and the excess liquid is shaken off, then all parts are air-dried.

It is important in accordance with this invention that the apparatus is completely free of O-rings or washers which, with packing, tend to wear. We have found suprisingly that by providing proper clearance between the rod 24, the inner tube 28 and the outer tube 30, that only minimal amounts of gas can escape from the body cavity, because of the close sliding fit—all without interfering with the smoothness and ease of operation of the ligating instrument 12.

The provision of compression spring 54, or any other equivalent resistance device, such as an air or gas cylinder, bellows or the like, is of considerable importance in that it assures the surgeon that the ligating instrument cannot discharge the occlusion rings 34, 36 prematurely. It is normal in the operation of the ligating instrument 12 for the surgeon to feel the increased resistance at the time that the forceps 26 have been completely withdrawn within the inner tube 28, and the surgeon must deliberately draw the manually actuated trigger 40 rearwardly against this known resistance in order to cause the release of an occlusion ring.

Although this invention has been described in connection with specific forms thereof, and with respect to specific steps of the methods herein involved, it will be appreciated that a wide variety of equivalents may be substituted for those specific elements shown and described herein, that certain features may be used independently of other features, and that certain parts and method steps may be reversed, all without departing from the spirit and scope of this invention as defined in the appended claims.

The following is claimed:

1. In a surgical ligating instrument for applying a plurality of elastic rings to one or more anatomical elements to be ligated, said rings having substantially the same width, the combination which comprises:
   (a) means on said instrument forming a support for a plurality of elastic rings, said support having an end adjacent which said rings may be stretched adjacent to and in substantial contact with each other;
   (b) actuating means movable in increments relative to said support for displacing a plurality of said rings toward said end of said support, one said increment being substantially equal to the width of one of said rings;
   (c) control means carried by said instrument for limiting said displacement substantially to the dimension of said increment after one of said rings, but not the adjacent ring, has been displaced off said end, and
   (d) said control means including manually adjustable means for subsequently adjusting said control means for permitting said actuating means to displace said adjacent ring off of said end.

2. The instrument defined in claim 1, wherein said support and said actuating means are axially relatively slidable elongated members.

3. The instrument defined in claim 1, wherein said control means includes an adjustably stop member.

4. The instrument defined in claim 2, wherein said actuating means includes a manually operable projection mounted on said elongated members for reciprocal movement axially thereon.

5. In a surgical ligating instrument for tubal ligation by the application of at least one elastic ring to an anatomical tube, the combination which comprises:
   (a) an elongated inner member having a forward end and a rearward end and having a grasping means constructed and arranged for grasping the anatomical tube to be ligated;
   (b) tube means adapted to fit slidably over said member (a), said tube means having a forward and rearward end with an insert disposed at said rearward end;
   (c) said tube means (b) having an outer cylindrical surface adapted to receive one or more elastic rings in a stretched condition;
   (d) a forwardly and rearwardly movable, manually reciprocal gripping means operatively connected to said member (a), said movable gripping means also being operatively connected to said tube means (b) upon the rearward end of member (a) contacting the insert of tube means (b) to effect sliding movement of said tube means (b);
   (e) means operative upon rearward movement of said member (a) relative to tube means (b) to actuate said grasping means to grasp the anatomical tube to be ligated and to draw it rearwardly into tube means (b);
   (f) an outer tube adapted to fit slidably over said tube means (b) and having a forward edge that is spaced rearwardly of the forward edge of said tube means (b), said outer tube (f) being operative upon retraction of said tube means (b) relative to said outer tube (f) to displace said elastic ring from the surface of the tube means (b) while said anatomical tube to be ligated extends into said tube means (b) thereby releasing said elastic ring into a position surrounding said anatomical tube and effecting tubal ligation;
   (g) a stationary gripping means attached to the rearward end of said outer tube (f) and cooperating with said movable gripping means (d) for effecting relative sliding movement of members (a), (b) and (f) back and forth along the axis of said member (f); and
   (h) a stop means disposed in a position to limit retraction of said tube means (b) relative to said outer tube (f) after displacement of an elastic ring off said tube means (b), said stop means including shiftable means independent of said outer tube (f) and said tube means (b) for shifting the effective position of said stop means to an alternative position which permits further retraction of said tube means (b) relative to said outer tube. (f).

6. The instrument defined in claim 5, wherein said movable gripping means (d) has concavely shaped forward and rearward surfaces for finger accomodation in both directions.

7. The instrument defined in claim 5, wherein said movable gripping means is mounted for reciprocation back and forth on said outer tube (f).

8. The instrument in accordance with claim 7, wherein a guide rod is attached to said stationary gripping means and extends forwardly and is slidably connected to said movable gripping means.

9. The instrument defined in claim 8, wherein said guide rod is parallel to and spaced from said outer tube.

10. The instrument defined in claim 5, wherein said stop means extends between said movable gripping means and said stationary gripping means.

11. The instrument defined in claim 5, wherein said stationary gripping means includes a curved hole adapted for operation by insertion of the surgeon's thumb.

12. The instrument defined in claim 11, wherein said stationary gripping means has a substantially flat rearward surface.

13. The instrument defined in claim 5, wherein a lighting means is provided surrounding said tube means (b).

14. A surgical ligation instrument in accordance with claim 5, wherein said movable gripping means is a finger grip.

15. A surgical ligating instrument in accordance with claim 5, wherein said movable gripping means is a push-pull trigger.

16. A surgical ligating instrument in accordance with claim 5, wherein said stationary gripping means is a thumb grip.

17. The surgical ligating instrument in accordance with claim 5, wherein said stationary gripping means is a pistol grip.

18. In a multiple-ring surgical ligating instrument for performing successive tubal ligations within the body by successive application of successive elastic rings, the combination which comprises:
   (a) a member having forceps means at its forward end and having a rearward end spaced from said forward end, (b) an elongated inner tube extending longitudinally over said member (a), (c) an elongated outer tube closely slidably fitted over said inner tube (b), and having a forward end that is spaced rearwardly of the forward end of inner tube (b) at a distance essentially equal to the sum of the thicknesses of multiple occluding rings to be mounted upon the forward end of said inner tube (b), (d) means for shifting said inner tube (b) rearwardly relative to said outer tube (c), and (e) stop means for limiting said shifting movement to a distance essentially equal to the thickness of a single occluding ring.

19. The instrument defined in claim 18, wherein said stop means (e) includes an adjusting means for adjusting the stop position to successive increments, which increments are spaced apart from each other at a distance which is essentially equal to the width of a single occluding ring.

20. The instrument defined in claim 19, wherein said means (d) is a movable gripping means, and wherein said stop means (e) is located outside said outer tube (c) and connected to said movable gripping means.

21. The instrument defined in claim 19, wherein said outer tube is connected to a stationary gripping means which includes a stop member engageable by said stop means to limit rearward movement of inner tube (b) rearwardly relative to outer tube (c).

22. The instrument defined in claim 19, wherein said stop means includes a yieldable means in the form of a substantially helical compression spring, said spring being in compressible force against said adjusting means.

23. The instrument defined in claim 18, including means for disassembling said member having forceps means and said tubes from each other for separate cleaning and sterilization.

24. The instrument defined in claim 18, wherein said member (a) includes a bore for connection to an optical viewing device having a viewing bore substantially parallel to and within said inner tube (b).

25. The instrument defined in claim 18, wherein said instrument is combined with and connected to an optical viewing device and wherein said optical viewing device includes a bore which has an inner diameter which forms a close sliding fit with the outer diameter of said outer tube (c).

26. The instrument defined in claim 18, wherein a pair of adjacent elastic occluding rings are stretched and maintained under tension upon the forward end of inner tube (b), and wherein the endmost said ring is expelled from inner tube (b) upon movement of inner tube (b) rearwardly into outer tube (c) by contact of said endmost ring with the adjacent ring which contacts the forward end of outer tube (c).

27. The instrument defined in claim 26, wherein said forward end of inner tube (b) projects forwardly of the front end of outer tube (c) by a distance equal to two thicknesses of said elastic occluding rings.

28. In a method of applying a plurality of elastic tubal ligation rings to one or more anatomical members to be ligated, the steps which comprise:

(a) stretching said plurality of rings over a common support, with essentially the same degree of stretch in each said ring, (b) positioning said rings substantially adjacent to each other on said support.

(c) moving both said rings through a controlled distance at least substantially equal to the width of one of said rings to displace one of said rings off the said support while maintaining the other said ring on said support, and subsequently, (d) incrementally moving the other ring a distance substantially equal to its width to displace said other ring from said support.

29. In a method of performing successive tubal ligations utilizing an applicator for successively attaching a plurality of elastic occluding bands, which applicator includes an elongated member having an anatomical tube grasping device at its forward end and having an inner tube on which said elastic bands are stretched substantially adjacent each other and having an outer tube the forward end of which is spaced rearwardly of the forward end of said inner tube, the steps which comprise:

(a) fitting a plurality of elastic rings onto said inner tube so that said rings are adjacent each other:

(b) grasping said anatomical tube in said grasping device;

(c) moving said grasping device and at least a part of said anatomical tube into the forward portion of said inner tube;

(d) drawing said inner tube rearwardly relative to said outer tube through a first distance sufficient for displacing the endmost of said rings off the forward end of said inner tube and contacting said endmost elastic ring onto the surface of said anatomical tube while displacing the other elastic ring to a position adjacent the end of said inner tube;

(e) releasing the resulting occluded tube;

(f) drawing another anatomical element tube into the forward position of said inner tube;

(g) drawing said inner tube rearwardly relative to said outer tube through a second distance, greater than said first distance, sufficient for displacing another ring therefrom and thereby occluding said other anatomical tube; and (h) releasing said other occluded anatomical tube.

30. A tubal ligation instrument for dispensing elastic rings onto anatomical elements comprising:

(a) a support member having a portion adapted for supporting a plurality of elastic rings mounted thereon;

(b) ring displacement member coaxial with and surrounding said support member along at least part of the length thereof, and adapted to discharge off said support member one or more elastic rings to a ligating position upon said anatomical elements;

(c) displacement means for moving said supporting member relative to said ring displacement member thereby to displace said elastic rings;

(d) shiftable limiting means independent of said displacement means, for limiting by a positive stop the relative movement of (a) and (b) to one of a plurality of predetermined limit positions, the maximum relative movement between (a) and (b) being different in each of said positions, said limiting means in a first position limiting said movement of (a) and (b) in a manner to limit to a predetermined number the elastic rings displaced off of said support member, at least one of said plurality of elastic rings remaining on said support member after the displacement, said limiting means in a subsequent shifted position permitting movement of (a) and (b) beyond the movement allowed by the first position, said subsequent shifted position adapted for permitting the displacement of one or more remaining elastic rings off of said support member.

31. The tubal ligation instrument in accordance with claim 30, wherein said support member is an inner tubular member and said ring displacement means is an outer tubular member extending longitudinally over said inner tubular member.

32. The tubal ligation instrument in accordance with claim 31, wherein said inner tubular member has a distal end from which said elastic rings are displaced off of said inner tubular member.

33. The tubal ligation instrument in accordance with claim 32, wherein said displacement means is a movable grip.

34. The tubal ligation instrument in accordance with claim 33, wherein said movable grip is slidable along said outer tubular member, and adapted for being in communication with said inner tubular member.

35. The tubal ligation instrument in accordance with claim 30, wherein said shiftable limiting means is adapted for being manually shiftable.

36. The tubal ligation instrument in accordance with claim 30, wherein said shiftable limiting means in said subsequent shifted position in a second position permitting movement of (a) and (b) beyond the movement allowed by the first position for limiting to a predetermined number the displacement of said elastic rings remaining on said inner tubular member.

37. The tubal ligation instrument in accordance with claim 36, wherein said predetermined number of elastic rings displaced off of said inner tubular member is one, with said shiftable limiting means in said first position.

38. The tubal ligation instrument in accordance with claim 37, wherein one of said elastic rings remains on said inner tubular member, with said shiftable limiting means in said first position.

39. The tubal ligation instrument in accordance with claim 38, wherein said predetermined number of remaining elastic rings displaced off of said inner tubular member is one, with said shiftable limiting means in said second position.

40. The tubal ligation instrument in accordance with claim 39, wherein said predetermined number of elastic rings displaced off of said inner tubular member is two, with said shiftable limiting means in said first position.

41. The tubal ligation instrument in accordance with claim 40, wherein two of said elastic rings remains on said inner tubular member, with said shiftable limiting means in said first position.

42. The tubal ligation instrument in accordance with claim 41, wherein said predetermined number of remaining elastic rings displaced off of said inner tubular member is two.

43. The tubal ligation instrument in accordance with claim 30, wherein said support member is of uniform diameter for providing said elastic rings with uniform support.

44. A tubal ligation instrument for disposing of elastic rings onto anatomical elements comprising:
   (a) means for supporting at a portion thereof said elastic rings,
   (b) means for displacing a predetermined number of elastic rings along said support means and concurrently displacing a predetermined number of elastic rings off said support means and upon said anatomical elements;
   (c) means for effecting a relative movement of said support means to said displacing means, thereby effecting the displacement of said elastic rings;
   (d) shiftable limiting means having a first position for limiting the relative movement of said support means to said displacing means in a manner that a predetermined number of elastic rings are displaced off of said support means, and concurrently a predetermined number of elastic rings remaining on said support means are displaced along said support means to a position for subsequent displacement thereof, said shiftable limiting means adapted to be shifted to a subsequent position which provides greater relative movement of said support means to said displacing means thereby providing displacement of a predetermined number of remaining elastic rings off of said support means.

45. The tubal ligation instrument in accordance with claim 44, wherein said support means is an inner tubular member and said ring displacement means is an outer tubular member extending longitudinally over said inner tubular member.

46. The tubal ligation instrument in accordance with claim 45, wherein said inner tubular member has a distal end from which said elastic rings are displaced off of said inner tubular member.

47. The tubal ligation instrument in accordance with claim 46, wherein said effecting means is a movable grip.

48. The tubal ligation instrument in accordance with claim 47, wherein said movable grip is slidable along said outer tubular member, and adapted for being in communication with said inner tubular member.

49. The tubal ligation instrument in accordance with claim 44, wherein said shiftable limiting means is adapted for being manually shiftable.

50. The tubal ligation instrument in accordance with claim 44, wherein said subsequent position of said shiftable limiting means in a second shifted position which permits movement of (a) and (b) beyond the movement allowed by the first position for limiting to a predetermined number the displacement of said elastic rings remaining on said inner tubular member.

51. The tubal ligation instrument in accordance with claim 50, wherein said predetermined number of elastic rings displaced off of said inner tubular member is one, with said shiftable limiting means in said first position.

52. The tubal ligation instrument in accordance with claim 51, wherein one of said elastic rings remains on said inner tubular member, with said shiftable limiting means in said first position.

53. The tubal ligation instrument in accordance with claim 52, wherein said predetermined number of remaining elastic rings displaced off of said inner tubular member is one.

54. The tubal ligation instrument in accordance with claim 50, wherein said predetermined number of elastic rings displaced off of said inner tubular member is two, with said shiftable limiting means in said first position.

55. The tubal ligation instrument in accordance with claim 54, wherein two of said elastic rings remains on said inner tubular member, with said shiftable limiting means in said first position.

56. The tubal ligation instrument in accordance with claim 55, wherein said predetermined number of remaining elastic rings displaced off of said inner tubular member is two, with said shiftable limiting means in said second position.

57. The tubal ligation instrument in accordance with claim 44, wherein said support member is of a uniform diameter for providing said elastic rings with uniform support.

58. A tubal ligation device for dispensing elastic rings onto anatomical elements comprising:
(a) a support means having a portion upon which a plurality of elastic rings may be mounted;
(b) a displacement means adapted for displacing a predetermined number of elastic rings along said support means and concurrently displacing a predetermined number of elastic rings off said support means, said elastic rings displaced off of said support means are disposed to a ligating position onto an anatomical elements;
(c) an effecting means for moving said support and displacement means relative to each other, thereby displacing said elastic rings along and off said support means.
(d) shiftable stop means for limiting the relative movement of said support and displacement means in a manner that a predetermined number of elastic rings are displaced off of said support means, and a predetermined number of said elastic rings are displaced along said support means and remaining thereon, said stop means shiftable for changing the limit of said relative movement in a manner to restrict to a predetermined number the displacement of elastic rings remaining on said support means.

59. A tubal ligation instrument for dispensing elastic rings onto anatomical elements comprising:
(a) a support means having a portion adapted for supporting a plurality of elastic rings mounted thereon, said support means having a distal end from which said elastic rings are displaced;
(b) a ring displacement means having a distal end for displacing along or off the distal end of said support means, one or more elastic rings by the relative movement of said support means to said displacement means;
(c) actuating means for moving said support means relative to said displacing means and thereby to displace said elastic rings;
(d) a shiftable limiting means for limiting the relative movement of said support and displacement means in a manner to restrict to a predetermined number the displacement of said elastic rings off of said support means, and concurrently displacing along said support means a predetermined number of said elastic rings which remain thereon.

60. A tubual ligation instrument for dispensing elastic rings onto an anatomical element comprising:
(a) a support member adapted to support, at its distal end, a plurality of elastic rings;
(b) a ring displacement member coaxial with and surrounding said support member along at least part of the length thereof, and adapted at its distal end to displace towards and beyond the distal end of said support member one or more elastic rings supported on said member;
(c) an actuating means for moving said displacement member relative to said support member and thereby effecting displacement of said elastic rings;
(d) shiftable limiting means independent of said displacement means, for limiting by a positive stop the movement of said support member relative to said ring displacement member to one of a plurality of predetermined limit positions, the maximum relative movement of said support member to said ring displacement member being different in each of said limit positions, said limiting means in a first position limiting said movement of said support to said displacement member in a manner to limit the number of elastic rings displaced beyond the distal end of said support member, said limiting means adapted to be shifted to a second position permitting relative movement of said support member and said ring displacement member beyond the movement allowed by the first position.

61. A tubal ligation instrument for disposing of elastic rings onto anatomical elements comprising:
(a) an inner tubular member adapted for supporting on at least a portion thereof a plurality of elastic rings, said inner tubular member having a distal end from which said elastic rings are displaced;
(b) an outer tubular member coaxial with and surrounding a portion of said inner tubular member, said outer tubular member having a distal end adapted for displacing along said inner tubular member and concurrently displacing off said inner tubular member said elastic rings;
(c) a movable gripping means adapted for effecting relative movement of said inner tubular member to said outer tubular member thereby causing the displacement of said elastic rings;
(d) a shiftable limiting means adapted for having a first position for limiting the relative movement of said inner tubular member to said outer tubular member in a manner to restrict to a predetermined number the displacement of said elastic rings off of the distal end of said inner tubular member, and concurrently at least one of said elastic rings is displaced toward the distal end of said inner tubular member and subsequently remains thereon, said shiftable limiting means further adapted for having a position which provides greater relative movement of said first position, thereby providing the displacement of one or more of said elastic rings remaining on said inner tubular member.

62. A method of ligating an anatomical element using an applicator for applying elastic rings to said element, said applicator having a support means for supporting said elastic rings, a displacement means coaxial with and slidable over said support means, said displacement means adapted for displacing a predetermined number of elastic rings off of said support means and concurrently displacing a predetermined number of elastic rings along said support means by the relative movement of said support means to said displacement means, and a shiftable limiting means for limiting the relative movement of said support means to said displacement means, comprising the steps of:
(a) grasping said anatomical element;
(b) disposing at least a portion of said grasped anatomical element into said support means;
(c) providing said limiting means in a position for limiting the relative movement of said support means to said displacement means, so that a predetermined number of elastic rings are capable of being displaced off said support means and concurrently a predetermined number of elastic rings are displaced along said support means;
(d) causing the relative movement of said support means to said displacement means thereby displacing said predetermined number of elastic rings off of said support means and onto said grasped anatomical element and concurrently displacing along said support means the predetermined number of elastic rings remaining on said support means;

(e) releasing said grasp and ligated anatomical element.

63. A method of operating a ligation instrument for disposing elastic rings onto anatomical element, said instrument having a means for supporting a plurality of said elastic rings, a means for displacing said elastic rings along and off said supporting means, and shiftable means for limiting the relative movement of said supporting means to said displacement means, comprising the steps of:
  (a) providing said limiting means in a first position for limiting the relative movement of said supporting means to said displacement means so that a predetermined number of elastic rings are displaced off of said support means and onto an anatomical element, and a predetermined number of said plurality of elastic rings remain on said support means and are disposed along said support means for subsequent displacement;
  (b) causing a first relative movement of said supporting means to said displacement means for displacing off and disposing along said support means said elastic rings;
  (c) shifting said limiting means to a second position for changing the limitation of said relative movement in a manner which permits a greater relative movement than in step (a) so that a predetermined number of said remaining elastic rings are displaced off of said support means;
  (d) causing a second relative movement of said supporting means to said displacement means to displace said predetermined number of said remaining rings off of said support means and onto another anatomical element.

64. A method of ligating a Fallopian tube of a female using an applicator for appying elastic rings to said tubes, said applicator having an inner tubular member for supporting said elastic rings, said inner tubular member having a distal end, an outer tubular member coaxial with and slidable over said inner tubular member, said outer tubular member adapted for displacing said elastic rings off said inner tubular member by the relative movement of said inner tubular member to said outer tubular member, and shiftable limiting means for limiting the relative movement of said inner tubular member to said outer tubular member, comprising the steps of:
  (a) grasping a Fallopian tube;
  (b) disposing at least a portion of said grasped Fallopian tube into said inner tubular member;
  (c) providing said limiting means in a position for limiting the relative movement of said inner tubular member to said outer tubular member, so that a predetermined number of elastic rings are capable of being displaced off said inner tubular member and concurrently a predetermined number of elastic rings are displaced along said inner tubular member toward said distal end and remain thereon;
  (d) causing relative movement of said inner tubular member to said outer tubular member thereby displacing the predetermined number of elastic rings off of said inner tubular member and onto said grasped Fallopian tube and concurrently displacing the predetermined number of elastic rings remaining on said inner tubular member toward said distal end of said inner tubular member, and
  (e) releasing said grasped and ligated Fallopian tube.

65. A method of ligating the Fallopian tubes of a female using an applicator for applying elastic rings to said tubes, said applicator having an inner tubular member for supporting said elastic rings, said inner tubular member having a distal end, an outer tubular member coaxial with and slidable over said inner tubular member, said outer tubular member adapted for displacing said elastic rings off said inner tubular member by the relative movement of said inner tubular member to said outer tubular member, and shiftable limiting means for limiting the relative movement of said inner tubular member to said outer tubular member, comprising the steps of:
  (a) grasping a Fallopian tube;
  (b) disposing at least a portion of said grasped Fallopian tube into said inner tubular member;
  (c) providing a limitation of the relative movement of said inner tubular member to said outer tubular member so that a predetermined number of elastic rings are capable of being displaced off said inner tubular member;
  (d) causing relative movement of said inner tubular member to said outer tubular member;
  (e) displacing a predetermined number of elastic rings off of said inner tubular member and onto said grasped Fallopian tube;
  (f) displacing, concurrently with step (e), the elastic rings remaining on said inner tubular member toward said distal end of said inner tubular member;
  (g) releasing said grasped and ligated Fallopian tube;
  (h) grasping said other Fallopian tube;
  (i) disposing at least a portion of said other Fallopian tube into said inner tubular member;
  (j) shifting said limiting means in a manner such that the relative movement of said inner tubular member to said outer tubular member is greater than in step (c).
  (k) causing relative movement of said inner tubular member to said outer tubular member;
  (l) displacing a predetermined number of elastic rings remaining on said inner tubular member after step (e), off of said inner tubular member and onto said grasped Fallopian tube;
  (m) releasing said ligated other Fallopian tube.

66. A method of ligating a vas deferens tube of a male using an applicator for applying elastic rings to said tubes, said applicator having an inner tubular member for supporting said elastic rings, said inner tubular member having a distal end, an outer tubular member coaxial with and slidable over said inner tubular member, said outer tubular member adapted for displacing said elastic rings off said inner tubular member by the relative movement of said inner tubular member to said outer tubular member, and shiftable limiting means for limiting the relative movement of said inner tubular member to said outer tubular member, comprising the steps of:
  (a) grasping a vas deferens tube;
  (b) disposing at least a portion of said grasped vas deferens tube into said inner tubular member;
  (c) providing said limiting means in a position for limiting the relative movement of said inner tubular member to said outer tubular member, so that a predetermined number of elastic rings are capable of being displaced off said inner tubular member and concurrently a predetermined number of elastic rings are displaced along said inner tubular member toward said distal end and remain thereon;
(d) causing relative movement of said inner tubular member to said outer tubular member thereby displacing the predetermined number of elastic rings off of said inner tubular member and onto said grasped Fallopian tube and concurrently displacing the predetermined number of elastic rings remaining on said inner tubular member toward said distal end of said inner tubular member;
(e) releasing said grasped and ligated vas deferens tube.

67. A method of ligating the vas deferens tubes of a male using an applicator for applying elastic rings to said tubes, said applicator having an inner tubular member for supporting said elastic rings, said inner tubular member having a distal end, an outer tubular member coaxial with and slidable over said inner tubular member, said outer tubular member adapted for displacing said elastic rings off said inner tubular member by the relative movement of said inner tubular member to said outer tubular member, and a shiftable limiting means for limiting the relative movement of said inner tubular member to said outer tubular member, comprising the steps of:
(a) grasping a vas deferens tube;
(b) disposing at least a portion of said grasped vas deferens tube into said inner tubular member;
(c) causing a limitation of the relative movement of said inner tubular member to said outer tubular member so that a predetermined number of elastic rings are capable of being displaced off said inner tubular member;
(d) causing relative movement of said inner tubular member to said outer tubular member;
(e) displacing a predetermined number of elastic rings off of said inner tubular member and onto said grasped vas deferens tube;
(f) displacing, concurrently with step (e), the elastic rings remaining on said inner tubular member toward said distal end of said inner tubular member;
(g) releasing said grasped and ligated vas deferens tube;
(h) grasping said other vas deferens tube;
(i) shifting said limiting means in a manner such that the relative movement of said inner tubular member to said outer tubular member is greater than in step (c).
(k) causing relative movement of said inner tubular member to said outer tubular member;
(l) displacing a predetermined number of elastic rings remaining on said inner tubular member after step (e), off of said inner tubular member and onto said grasped vas deferens tube;
(m) releasing said ligated other vas defernes tube.

68. In a surgical ligating instrument for tubal ligation by the application of at least one elastic ring to an anatomical tube, the combination which comprises:
(a) an elongated inner member having a forward end and a rearward end and having an anatomical tube grasping means constructed and arranged for grasping the anatomical tube to be ligated;
(b) tube means adapted to fit slidably over said member (a), said tube means having a forward and rearward end with an insert disposed at said rearward end;
(c) said tube means (b) having an outer cylindrical surface adapted to receive one or more elastic rings in a stretched condition:
(d) a forwardly and rearwardly movable, manually reciprocable gripping means operatively connected to said member (a), said movable gripping means also being operatively connected to said tube means (b) upon the rearward end of member (a) contacting the insert of tube means (b) to effect sliding movement of said tube means (b);
(e) means operative upon rearward movement of said member (a) relative to tube means (b) to actuate said grasping means to grasp the anatomical tube to be ligated and to draw it rearwardly into tube means (b);
(f) an outer tube adapted to fit slidably over said tube means (b) and having a forward edge that is spaced rearwardly of the forward edge of said tube means (b), said outer tube (f) being operative upon retraction of said tube means (b) relative to said outer tube (f) to displace said elastic ring from the surface of tube means (b) while said anatomical tube to be ligated extends into said tube means (b), thereby releasing said elastic ring into a position surrounding said anatomical tube and effecting tubal ligation;
(g) a stationary gripping means attached to the rearward end of said outer tube (f) and cooperating with said movable gripping means (d) for effecting relative sliding movement of members (a), (b) and (f) back and forth along the axis of said member (f); and
(h) a stop means extending between said movable gripping means and said stationary gripping means to limit retraction of said tube means (b) after displacement of an elastic ring off of said tube means (b), said stop means including a shiftable means for shifting the effective position of said stop means, thereby varying the distance through which said tube means (b) may be retracted relative to said outer tube (f), said stop means includes a sleeve mounted in said movable gripping means and slidably surrounding said outer tube (f).

69. The instrument defined in claim 68, wherein said sleeve is in continuous contact with a spring which is substantially helical and which is mounted within said movable gripping means.

70. The instrument defined in claim 69, wherein said movable gripping means includes a hollowed body portion including a pair of longitudinally spaced stops, wherein said spacing sleeve is within said body and includes a manually adjustable handle extending outside said movable gripping means body, and wherein said manually engageable handle is urged by said spring in the opposite direction of said stops.

* * * * *

UNITED STATES PATENT AND TRADEMARK OFFICE
CERTIFICATE OF CORRECTION

PATENT NO. : 4,226,239
DATED : October 7, 1980
INVENTOR(S) : Todd J. Polk and Francis E. McGowan It is certified that error appears in the above-identified patent and that said Letters Patent are hereby corrected as shown below:

Column 1, line 35, "supra-public" should read -- suprapubic --.

Column 5, line 22, "supra-public" should read -- suprapubic --.

Column 6, line 13, after "bore", "38" should read -- 38' --.

Column 6, line 62, before "of pistol", "46=" should read -- 46' --.

Column 8, line 13, "FIG. 5" should read -- FIG. 5. --.

Column 17, line 52, "tubual" should read -- tubal --.

Column 19, line 40, "appying" should read -- applying --.

Column 21, line 57, "defernes" should read -- deferens --.

Signed and Sealed this

Seventeenth Day of February 1981

[SEAL]

Attest:

RENE D. TEGTMEYER

Attesting Officer    Acting Commissioner of Patents and Trademark